(12) United States Patent
Nair

(10) Patent No.: US 7,220,825 B2
(45) Date of Patent: May 22, 2007

(54) POLYPEPTIDE USEFUL FOR A NON-INVASIVE TEST FOR INFLAMMATORY BOWEL DISEASE

(76) Inventor: Padmanabhan P. Nair, 4520 Hemlock Coneway, Ellicott City, MD (US) 21042

( * ) Notice: Subject to any disclaimer, the term of this patent is extended or adjusted under 35 U.S.C. 154(b) by 521 days.

(21) Appl. No.: 10/652,666

(22) Filed: Aug. 29, 2003

(65) Prior Publication Data

US 2004/0146947 A1   Jul. 29, 2004

Related U.S. Application Data

(63) Continuation-in-part of application No. 09/755,234, filed on Jan. 8, 2001, now Pat. No. 6,645,729.

(51) Int. Cl.
*A61K 38/00*   (2006.01)

(52) U.S. Cl. .................................................. 530/326
(58) Field of Classification Search .................... None
See application file for complete search history.

(56) References Cited

U.S. PATENT DOCUMENTS 5,459,239 A * 10/1995 O'Neill et al. .............. 530/327
6,048,850 A *  4/2000 Young et al. ................ 514/183

* cited by examiner

*Primary Examiner*—Phillip Gambel
*Assistant Examiner*—Zachary Skelding
(74) *Attorney, Agent, or Firm*—Mishrilal Jain

(57) ABSTRACT

A non-invasive method of testing for inflammatory bowel disease using a domain specific monoclonal antibody is described. A unique 18 residue amino acid sequence overexpressed in COX-2 has been identified for making and using the monoclonal antibody.

4 Claims, 1 Drawing Sheet

SEQUENCE LISTING

<160> NUMBER OF SEQ ID NOS: 1

<210> SEQ ID NO 1
<211> LENGTH: 18
<212> TYPE: PRT
<213> ORGANISM: Homo sapiens

<400> SEQUENCE: 1

Leu Cys Ala Val Leu Ala Leu Ser His Thr Ala Asn Pro Cys Cys Ser
1               5                   10                  15

His Pro

POLYPEPTIDE USEFUL FOR A NON-INVASIVE TEST FOR INFLAMMATORY BOWEL DISEASE

This is a continuation in Part of patent application Ser. No. 09/755,234 filed Jan. 8, 2001 now U.S. Pat. No. 6,645,729).

FIELD OF THE INVENTION

This invention relates to providing a product and method for diagnosing inflammatory bowel disease (IBD). More particularly, this invention relates to providing domain-specific monoclonal antibody to cyclooxygenase-2 (COX-2) useful in diagnosing IBD.

BACKGROUND OF INVENTION

Inflammatory Bowel Disease (IBD) remains an intractable chronic disease affecting more than a quarter of a million individuals in the United States alone. The disease is characterized by a persistent inflammatory response that is central to the pathophysiology of this condition. At the present time endoscopy is the accepted procedure for confirming a diagnosis of IBD. However, endoscopy is an invasive and expensive procedure for screening subjects and for frequent follow-up of established cases. Therefore, providing a non-invasive reliable test for diagnosing IBD remains a desirable goal.

Recently it has been shown that colonic and inflammatory cells can be recovered in a viable state from stool samples and examined for markers of colonic inflammation and disease and that expression of COX-2 in these exfoliated cells is of diagnostic significance in IBD (U.S. Pat. Nos. 6,335,193 and 6,534,280). However, heretofore specific assessment of COX-2 expression in exfoliated colonocytes from stools as a marker of IBD was not known.

SUMMARY OF INVENTION

It is, therefore, an object of the present invention to provide a method and product for reliable testing of IBD.

It is a further object of the present invention to identify a region closer to the 5' end of the COX-2 gene that is consistently overexpressed and, therefore, can serve as a marker for IBD as determined by Reverse Transcriptase-Polymerase Chain Reaction (RT-PCR).

It is another object of the present invention to prepare an antigenic translational polypeptide based on said overexpressed segment of the COX-2 gene.

It is an additional object of the present invention to provide a domain-specific monoclonal antibody to COX-2 useful in testing for IBD.

Various other objects and advantages of the present invention will become evident from the following brief description of the drawings and from the detailed description of the invention.

DETAILED DESCRIPTION OF THE INVENTION

Figure 1:
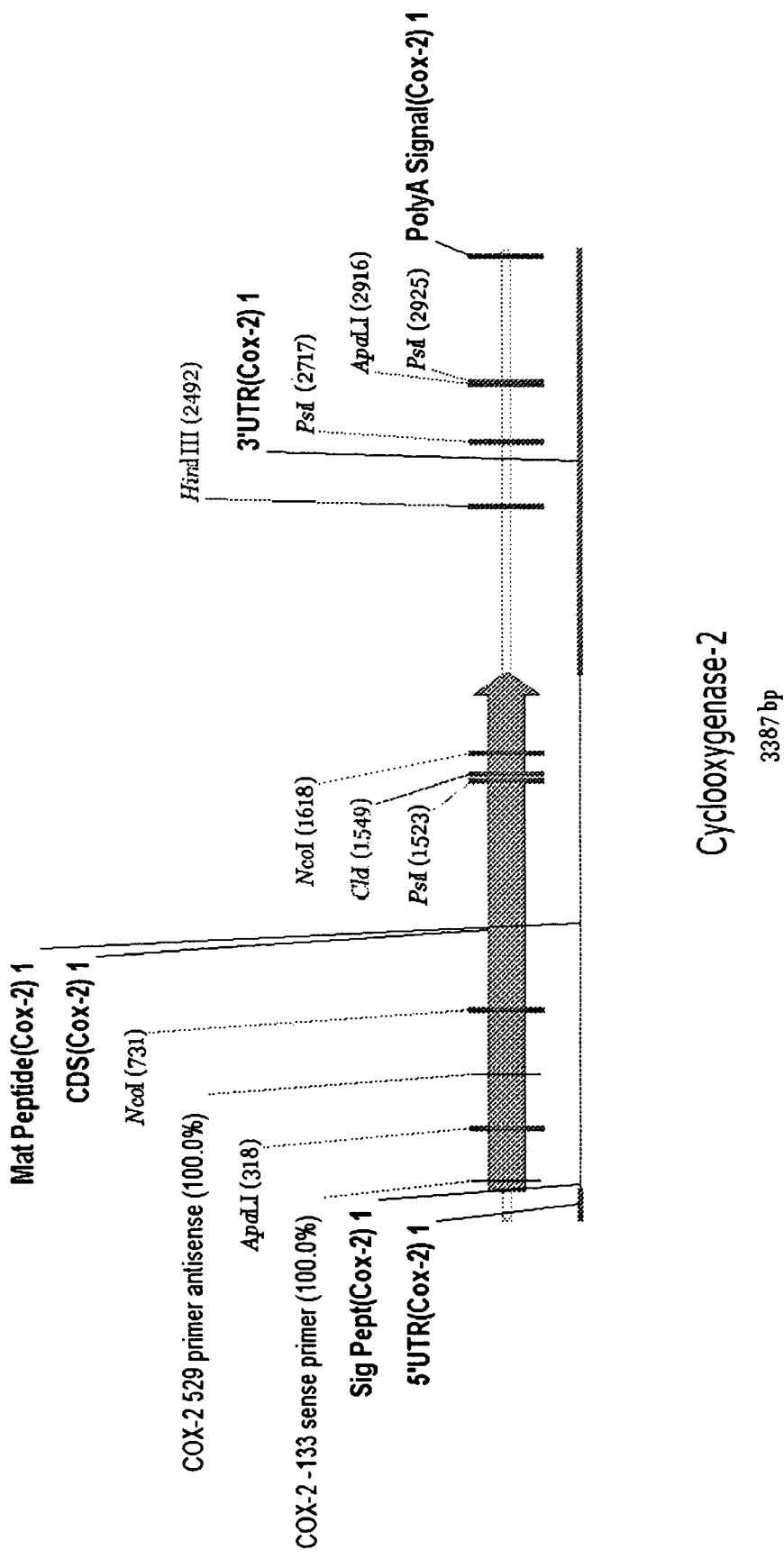
FIG. 1 is a schematic representation showing base pair (bp) span of the COX-2 gene.

The above and various other objects and advantages of the present invention are achieved by identifying a specific domain in the COX-2 gene that is overexpressed in IBD, then preparing an immunogenic translational polypeptide based on this domain and then producing a monoclonal antibody that specifically binds to this domain.

It has been discovered that this domain in the COX-2 gene spans the bp region 133-529 (see FIG. 1) yielding a PCR amplicon of 397 bp. It has been further discovered that a translational polypeptide expressed from bp 119-172 overlaps the above mentioned overexpressed fragment and a monoclonal antibody prepared against this polypeptide serves as a specific reagent for testing screening, diagnosing or follow up of IBD course after or during treatment.

As should be well known to one of ordinary skill in the art to which this invention belongs, monoclonal antibodies from hybridoma clones offer several advantages over polyclonal antibodies derived from conventionally prepared antiserum prepared by immunization of animals. A few such advantages are listed below.

(1) Monoclonal antibodies are directed against a single epitope (antigenic determinant) on a molecule, as compared to conventional polyclonal antiserum, which contains a population of antibodies.

(ii) Monoclonal antibodies are homogenous with respect to affinity and specificity. Conventional antiserum contains antibodies which vary greatly in affinity.

(iii) The hybridomas can be frozen and can produce an unlimited supply of monoclonal antibodies when recovered as desired at a later date.

Experimental Procedures

It should be understood that unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the methods and materials described herein are preferred. Unless mentioned otherwise, the techniques employed or contemplated herein are standard methodologies well known to one of ordinary skill in the art. The materials, methods and examples are only exemplary and not limiting.

1. Synthesis of the Domain-Specific Peptide:

The following 18-amino acid polypeptide residue of the present invention representing the translational product of the 119-172 bp domain in the COX-2 gene was used as the immunogen. The amino acid sequence of said polypeptide of the present invention is as follows:

Leu-Cys-Ala-Val-Leu-Ala-Leu-Ser-His-Thr-Ala-Asn-Pro-Cys-Cys-Ser-His-Pro  (SEQ ID NO:1)

This fragment is unique in that it does not share any sequence homology to the COX-1 protein in humans. This unique polypeptide was synthesized using the conventional FMOC method (Carpino et al, 1972. J. Org. Chem. 37:3404-3409).

2. Conjugation of Peptide with Keyhole Limpet Hemocvanin (KLH)

The polypeptide was conjugated to the carrier protein KLH (Green, N. et al 1982. Cell 28:477-487) through a heterobifunctional reagent m-maleimidobenzoyl-N-hydroxysuccinimide ester (MBS) according to the procedure described below:
   i. The carrier protein KLH was dissolved at a concentration of 10 mg/ml in 0.1 M phosphate buffer, PH 7.2:
   ii. The crosslinking reagent (MBS) was prepared in dimethylformamide at a concentration of 25 mg/ml;
   iii. MBS was added to the KLH solution and the reaction mixture was stirred at ambient room temperature (~22° C.) about for 30 min;
   iv. The activated KLH was separated from free MBS using Sephadex G-25 in phosphate buffer;
   v. The peptide was dissolved in 0.1 M phosphate buffer and mixed with activated KLH separated in step iv and allowed to remain stirred at ambient room temperature for about 30 minutes. The coupled protein conjugate was then purified by standard gel filtration.

One hundred μg of the conjugate was mixed with the Complete Freund's adjuvant (CFA) and injected in 5 balb/c mice. Booster dose of 50 μg mixed with incomplete Freund's adjuvant (IFA) was given to all the 5 mice after 2 and 4 weeks. Blood serum from the mice was obtained following standard procedure well known to a skilled artisan in the art to which this invention belongs.

3. Testing the Performance of Antiserum:

The activity of the antiserum was checked by the determination of the titer using ELISA. The protocol is described below:
   a. The peptide was conjugated with Bovine Serum Albumin (BSA) using MBS as described in the previous section. The conjugate was diluted with phosphate buffered saline (PBS) to a final concentration of 1.0 μg/ml and used to coat 96 well ELISA plates (100 μl/well).
   b. The plate was covered and incubated overnight at 4 C. The plate was washed with washing buffer twice (PBS/ 0.5% Tween 20, 200 μl/well).
   c. The wells were blocked with 1% BSA in PBS. 200 μl/well, at ambient room temperature for 2 hours.
   d. The plates were emptied and then the testing antibody was added at various concentrations, 100 μl/well.
   e. The plate was incubated at 37° C. for about 1.5 hours. The plate was washed 5 times with washing buffer, 200 μl/well.
   f. The Horse Radish Peroxidase (HRP) conjugated secondary antibody (100 μl/well) was added and incubated at 37° C. for about 30 minutes.
   g. The plates were washed 5 times with washing buffer, 200 μl/well.
   h. TMB (3',3',5',5'-tetramethyl benzidine) substrate was added (100 μl/well) and the plate was incubated at room temperature for about 30 minutes. Then the reaction was stopped by the addition of 100 μl of stopping solution (1.0M HCl).
   i. The absorbance was read at 450 nm using an ELISA plate reader. After 4 weeks the titer for the sera from all the 5 mice was about 1:256,000(absorbance units at 450 nm was >0.2) which was considered to be a good titer value. Thus, at this stage two of the mice were selected for fusion with myeloma cell line SP2/0-Ag14.

4. Fusion and Colony Screening
   1. Two mice were selected for final boosts at 3-5 days before cell fusion.
   2. The mice were euthanized to remove the spleens and spleen cells were harvested. The harvested splenocytes were fused with myeloma cells (cells ratio of 5:1 ) by standard polyethylene glycol (PEG) method using the fusion culture medium containing hypoxanthine, aminopterin and thymidine selection medium (HAT). The fused cells were cloned in 24-well plates by starting with $0.5\text{-}1.0 \times 10^5$ cells. The cell fusion efficiency was above average (50%)which was considered to be successful.
   3. After 10 days of fusion the hybridoma clones were screened by standard ELISA procedure using peptide-BSA as coating antigen.
   4. The positive parental hybridoma clones were expanded, re-tested using ELISA procedure using peptide-BSA conjugate to confirm the reactivity. The selected clones were also isotyped (see Table 1).

TABLE 1

ELISA screening and isotyping of Parental hybridoma Cell lines

| Parental Clone# | isotype | A450, peptide-BSA | A450, BSA | A450, free peptide | Subcloning |
|---|---|---|---|---|---|
| 1. 5E6 | IgG1 | 2.000 | 0.398 | 1.399 | Subcloned |
| 2. 7A6 | IgG1 | 1.737 | 0.086 | 0.475 | |
| 3. 7C11 | IgG1 | 1.540 | 0.075 | 0.491 | |
| 4. 12H7 | IgG1 | 0.326 | 0.274 | 0.566 | Subcloned |
| 5. 14D4 | IgG1 | 1.408 | 0.078 | 0.560 | Subcloned |
| 6. 12H1 | IgG1 | 1.118 | 0.078 | 0.846 | Subcloned |

Six clones, as shown above, were selected and frozen in liquid nitrogen. Four clones 5E6, 12H7, 14D4 and 12H1 were further subcloned using limiting dilution. Finally, six stable cell lines were identified as shown in Table 2. All of them were isotyped using commercially available ELISA kit from Southern Biotech and were identified as IgG1/kappa chain type.

These cell lines are tested for their reactivity against native COX-2 protein using a colon cancer cell line (LS-180 cell line).

Having described the procedure for obtaining domain-specific monoclonal antibody against IBD, it should be noted that given the identification and preparation of the unique 18 residue antigenic polypeptide of the present invention, one of ordinary skill in the art can make and use the monoclonal antibody following well established standard procedures known in the art for preparation of monoclonal antibodies. In other words, what is crucial and critical is the identification of the 18 residue polypeptide overexpressed in IBD. Once the immunogen, i.e., the 18 residue antigen is at hand, the preparation and obtaining the monoclonal antibody becomes a routine standard process.

TABLE 2

Final selection of Subclones from parental Hybridoma Cell lines

| | Parental Clone# | Subclonal# | isotype |
|---|---|---|---|
| 1. | 5E6 | NIDCX.5E6.G8 | IgG1/k |
| 2. | | NIDOX.5E6.H8 | IgG1/k |
| 3. | 14D4 | NIDCX.14D4.H1.D12 | IgG1/k |
| 4. | | NIDCX.14D4.H1.H10 | IgG1/k |
| 5. | 10H1 | NIDCX.10H1.D6.A8.B4 | IgG1/k |
| 6. | | NIDCX.10H1.D6.A8.D3 | IgG1/k |

All clones listed herein produce the domain-specific antibody, which bind specifically with COX-2 protein in colonocytes and inflammatory cells isolated from IBD patients as determined by ELISA assay and are useful in testing, screening or diagnosing IBD and for follow up of the course of the disease after or during treatment thereof.

A method of testing for inflammatory bowel disease, comprises the steps of:
  (i) isolating colonocytes and inflammatory cells from a stool sample (see U.S. Pat. No. 6,335,193); then
  (ii) reacting said cells with a monoclonal antibody having binding affinity to a specific domain of cyclooxygenase-2, said domain having an amino acid sequence: Leu-Cys-Ala-Val-Leu-Ala-Leu-Ser-His-Thr-Ala-Asn-Pro-Cys-Cys-Ser-His-Pro (SEQ ID NO:1; a positive reaction of said monoclonal antibody with said isolated cells being indicative of inflammatory bowel disease.

Of course, having learnt the teachings of the present invention, one skilled in the art may vary the processes in different ways to meet the objectives of the present invention.

Example embodiments of the present invention have now been described in accordance with the above advantages. It will be appreciated that these examples are merely illustrative of the invention and not limitations thereof. Many variations and modifications will be apparent to those skilled in the art and all such modifications and variations are included within the purview and scope of the appended claims.

The invention claimed is:

1. A synthetic polypeptide of the amino acid sequence:

Leu-Cys-Ala-Val-Leu-Ala-Leu-Ser-His-Thr-Ala-Asn-Pro-Cys-Cys-Ser-His-Pro  (SEQ ID NO:1).

2. The polypeptide of claim 1, wherein the amino acid sequence of said polypeptide is employed as an antigen to prepare an antibody.

3. The polypeptide of claim 2, wherein said antibody binds to a specific cyclooxygenase-2 domain overexpressed in inflammatory bowel disease.

4. The polypeptide of claim 3, wherein said antibody is reacted with inflammatory cells isolated from a stool sample, a positive reaction of said antibody with said cells being indicative of inflammatory bowel disease.

* * * * *

UNITED STATES PATENT AND TRADEMARK OFFICE
CERTIFICATE OF CORRECTION

| | |
|---|---|
| PATENT NO. | : 7,220,825 B2 |
| APPLICATION NO. | : 10/652666 |
| DATED | : May 22, 2007 |
| INVENTOR(S) | : Padmanabhan P. Nair |

It is certified that error appears in the above-identified patent and that said Letters Patent is hereby corrected as shown below:

Col. 1, line 3 insert

--This invention was made in part with government support under a National Institute of Diabetes, and Digestive and Kidney Diseases SBIR grant R44DK56567. The Government may have certain rights in the invention.--

Signed and Sealed this

Thirty-first Day of July, 2007

JON W. DUDAS
*Director of the United States Patent and Trademark Office*